(12) United States Patent
Davidson et al.

(10) Patent No.: US 9,511,024 B2
(45) Date of Patent: Dec. 6, 2016

(54) AMINO LIPIDS, THEIR SYNTHESIS AND USES THEREOF

(75) Inventors: Gary Davidson, Graben-Neudorf (DE); Pavel Levkin, Eggenstein-Leopoldshafen (DE); Linxian Li, Eggenstein-Leopoldshafen (DE); Yi Su, Eggenstein-Leopoldshafen (DE); David Zahner, Ladenburg (DE)

(73) Assignee: INCELLA GMBH, Eggenstein-Leopoldshafen (DE)

( * ) Notice: Subject to any disclaimer, the term of this patent is extended or adjusted under 35 U.S.C. 154(b) by 242 days.

(21) Appl. No.: 14/124,468

(22) PCT Filed: May 15, 2012

(86) PCT No.: PCT/EP2012/002101
§ 371 (c)(1),
(2), (4) Date: Feb. 18, 2014

(87) PCT Pub. No.: WO2012/167869
PCT Pub. Date: Dec. 13, 2012

(65) Prior Publication Data
US 2014/0187614 A1    Jul. 3, 2014

(30) Foreign Application Priority Data

Jun. 7, 2011 (EP) .................................. 11004610

(51) Int. Cl.
| | |
|---|---|
| *A61K 9/127* | (2006.01) |
| *C07C 317/44* | (2006.01) |
| *C07C 323/60* | (2006.01) |
| *C07D 295/125* | (2006.01) |
| *C07D 295/185* | (2006.01) |

(52) U.S. Cl.
CPC ........... *A61K 9/1272* (2013.01); *C07C 317/44* (2013.01); *C07C 323/60* (2013.01); *C07D 295/125* (2013.01); *C07D 295/185* (2013.01); *Y10T 428/2982* (2015.01)

(58) Field of Classification Search
CPC ....................................................... A61K 31/53
See application file for complete search history.

(56) References Cited

U.S. PATENT DOCUMENTS

| | | |
|---|---|---|
| 2010/0055169 A1 | 3/2010 | Dande et al. |
| 2013/0197189 A1* | 8/2013 | Aimetti .................. C07K 1/113 530/321 |

FOREIGN PATENT DOCUMENTS

| | | |
|---|---|---|
| CN | 1180697 | 5/1998 |
| EP | 0846680 A | 10/1997 |
| WO | 01/42200 A1 | 6/2001 |

OTHER PUBLICATIONS

Andrew D. Miller, "Cationic Liposomes for Gene Therapy," Angewandte Chemie, International Edition, Aug. 1998, pp. 1768-1785, vol. 37, No. 13.
International Search Report and Written Opinion of International Searching Authority for PCT/EP2012/002101 dated Jul. 26, 2012.

* cited by examiner

*Primary Examiner* — Benjamin Packard
(74) *Attorney, Agent, or Firm* — Ryan, Mason & Lewis, LLP (57) ABSTRACT

The present invention provides new amino lipids and a convenient method for synthesizing these compounds. These (cationic) amino lipids have good properties as transfection agents. The method is an economic versatile two step synthesis allowing the preparation of various amino lipids thus leading to the assembly of a combinatorial library of transfection agents. Moreover, the present invention provides lipid particles (liposomes) containing said amino lipids and their use for delivering bioactive agents into cells. The invention encompasses also the use of lipid particles containing the cationic amino lipids as medicament.

22 Claims, 2 Drawing Sheets

| Transfection reagent | reagent A | | lipidoid #29 |
|---|---|---|---|
| siRNA | Con | Irp6 | Irp6 |

LRP6 →
loading →

B

| transfection reagent | reagent A | | #29 | | #35 | |
|---|---|---|---|---|---|---|
| con siRNA | + | | + | | + | |
| lrp6 siRNA | | + | | + | | + |

LRP6 b-Actin

AMINO LIPIDS, THEIR SYNTHESIS AND USES THEREOF

TECHNICAL FIELD

The present invention provides new amino lipids and their synthesis. These (cationic) amino lipids have good properties as transfection agents. They can be used to produce lipid particles, especially liposomes, allowing the delivery of bioactive agents into cells. The simplicity of the synthesis allows the development of a combinatorial library of amino lipids in a kit-like manner. The compounds contained in this library can be screened for particular properties in particular for the transfection of various cell lines. The invention encompasses also the use of lipid particles containing the (cationic) amino lipids as medicament.

BACKGROUND

Of the various reagents used to transfect cells with bioactive agents such as nucleic acids, those based on liposome mediated delivery are widely acknowledged to be the most effective. This is due mostly to their efficiency and ease of use. Liposomes are artificially prepared spherical vesicles made of lipid bilayer. To deliver the molecules to sites of action, the lipid bilayer can fuse with other bilayers such as a cell membrane, thus delivering the liposome contents inside a cell.

Liposomes are used for drug delivery due to their unique properties. A liposome encapsulates a region of aqueous solution inside a hydrophobic membrane; dissolved hydrophilic solutes cannot readily pass through the lipids. Hydrophobic chemicals can be dissolved into the membrane, and in this way liposome can carry both hydrophobic molecules and hydrophilic molecules. Liposomes can be combined with bioactive agents such as drugs, nucleic acids, peptides etc., and used to deliver these agents for the regulation of a cells biochemical pathway. This opens possibilities for new treatments of diseases.

Gershon et al. (Gershon H, et al. Mode of formation and structural features of DNA-cationic liposome complexes used for transfection. Biochemistry. 1993, 32:7143-7151) state that nanoparticles which are formed between cationic liposomes and nucleic acids represent an efficient vehicle for delivery of DNA and RNA into cell. Cationic liposomes bind initially to DNA molecules to form clusters of aggregated vesicles along the nucleic acids. At a critical liposome density, two processes occur, DNA-induced membrane fusion and liposome-induced DNA condensation. The DNA condensation leads to the formation of condensed structures which can be completely encapsulated with the fused lipid bilayers in a fast, highly cooperative process.

For delivery of negatively charged nucleic acid, cationic lipids are the most effective transfection agents. Cationic lipids represent a promising class of synthetic materials for DNA delivery. To date, there are several commercialized cationic lipids but the number of cationic lipids for safe and effective delivery of genes is still limited.

In "Cationic liposomes for gene therapy" (Miller A D, Angew Chem Int Ed. 1998, 37:1768-1785) most of the commonly used and commercially available transfection agents are described. However, conventional lipid synthesis typically requires individually optimized, multiple-step synthesis, including time-intensive procedures such as chemical protection and deprotection, use and removal of catalysts, solvent exchanges and purification.

WO 01/42200 describes examples of cationic amphiphilic compounds and their use in pharmaceutical compositions as transfection agents. The compounds disclosed in this document are made in a time consuming multiple-step synthesis.

Cationic lipids need to be combined with natural phospholipids (referred to as helper lipids) to form liposomes that can be more efficiently incorporated into cell membranes. By combining liposomes with DNA or drugs, which alone cannot diffuse through the membrane of the target cell, they can be (indiscriminately) delivered past the lipid bilayer. The use of liposomes for transformation or transfection of DNA into a host cell is known as lipofection.

Although liposomal reagents represent the state of the art with respect to cell transfection agents, they have the following drawbacks:

1. Many cell lines (such as primary cells) cannot be effectively transfected at the moment, even with liposomal reagents.
2. They are relatively difficult and expensive to synthesise, often resulting in high price for end-users.

As a consequence of the second point, many laboratories use less efficient, cheaper alternatives for transfection (e.g. calcium phosphate). There is a concrete requirement for new transfection agents that are easy to synthesize and which have good transfection yields for a wide variety of cell types. As an alternative, it would be helpful to dispose an easy combinatorial synthesis of transfection agents allowing the production of a variety of different compounds.

OBJECTIVES OF THE INVENTION

To overcome the disadvantages of the state of the art, it is an objective of the present invention to provide novel cationic amino lipids and a method for their synthesis. The method should be generic, economic and easy to perform. This generic method allows the development of a library of cationic amino lipids. Generation of such lipid libraries (containing of hundreds of different lipid molecules) greatly enhances the identification of lipids harbouring optimal transfection reagent properties.

It is a further objective of the present invention to provide lipid particles, especially liposomes, containing said cationic amino lipids. In particular, these lipid particles or liposomes should be able to deliver bioactive agents through cell membranes. Another objective is the use of said lipid particles or liposomes for treatment of diseases.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Exemplar embodiments of the invention will now be discussed in further detail. This invention may, however, be embodied in many different forms and should not be construed as limited to the embodiments set forth herein.

The invention provides novel amino lipids with the following general formula (I):

(I)

wherein $R^1$ and $R^2$ are the same or different and independently $C_6$-$C_{24}$ alkyl, $C_6$-$C_{24}$ alkenyl, $C_6$-$C_{24}$ alkynyl, or $C_6$-$C_{24}$ acyl, which can be optionally substituted with a $C_1$-$C_6$ hydrocarbyl group, $X^1$ and $X^2$ are the same or different, either S or S=O or S(=O)$_2$, Y is either an amide, an ester or a heterocyclic amide of the formula wherein k and l are integers from 0 to 2,
$R^3$ and $R^4$ are either the same or different and independently $C_1$-$C_{12}$ alkyl, $C_1$-$C_{12}$ alkenyl, or $C_1$-$C_{12}$ alkynyl, wherein alkyl, alkenyl or alkynyl may be optionally substituted with a $C_1$-$C_6$ hydrocarbyl group, or $R^3$ and $R^4$ may join to form an optionally substituted heterocyclic ring of 3 to 10 atoms and 0 to 6 heteroatoms chosen from nitrogen, thiol and oxygen,
$R^5$ is either absent or is hydrogen or $C_1$-$C_{12}$ alkyl to provide a quaternary amine,
m is an integer from 1 to 12 and n is an integer from 2 to 12.

In a preferred embodiment of the invention, $R^1$ and $R^2$ are the same or different and independently $C_6$-$C_{24}$ alkyl, more preferred, $R^1$ and $R^2$ are the same $C_6$-$C_{18}$ alkyl.

Also, the present invention provides amino lipids of the general formula (II):

(II)

$R^1$ and $R^2$ are the same $C_6$-$C_{18}$ alkyl
Y is either an amide, an ester or a heterocyclic amide of the formula wherein k and l are integers from 0 to 2,
$R^3$ and $R^4$ are either the same or different $C_1$-$C_{12}$ alkyls, wherein alkyl may be optionally substituted with a $C_1$-$C_6$ hydrocarbyl group, or $R^3$ and $R^4$ may join to form an optionally substituted heterocyclic ring of 3 to 10 atoms and 0 to 6 heteroatoms chosen from nitrogen, thiol and oxygen,
m is an integer from 1 to 12 and n is an integer from 2 to 12.

In another preferred embodiment of the invention Y is an amide.

In a preferred embodiment of the compounds according to the formulas (I) or (II),
n and m are independently integers 2 or 3.

The most preferred embodiments correspond to the structures of formula (IIIa), (IIIb) or (IIIc)

(IIIa)

(IIIb)

(IIIc)

wherein $R^1$ and $R^2$ are the same $C_{11}$-$C_{12}$ alkyls,
$R^3$ and $R^4$ are the same $C_1$-$C_2$ alkyls,
m is an integer from 1 to 2, n is an integer from 2 to 3.

The present invention provides a method to synthesize amino lipids as defined in claims 1 to 4. The method represents the first parallel synthesis of large libraries of ionisable cationic amino lipids based on thiol-yne chemistry in liquid-phase combinatorial synthesis without chromatography purification comprising the following steps:

The first step is reaction of alkynes of the general formula (IVa), (IVb) or (IVc)

(IVa)

(IVb)

(IVc)

wherein n is an integer from 2 to 12,
with compounds of the general formula, HS—$R^1$ and HS—$R^2$,
wherein $R^1$ and $R^2$ are the same or different and independently $C_6$-$C_{24}$ alkyl, $C_6$-$C_{24}$ alkenyl, $C_6$-$C_{24}$ alkynyl, or $C_6$-$C_{24}$ acyl, which can be optionally substituted with a

$C_1$-$C_6$ hydrocarbyl group, under either UV-irradiation or using a radical initiator, to yield a compound of the general formula (Va), (Vb) or (Vc)

wherein n, $R^1$ and $R^2$ are defined as above,

This reaction is conducted via a radical mechanism. Chemical radical sources can be added to start the reaction or it can be simply conducted under sunlight. In a preferred embodiment the reaction is started by UV irradiation.

The second step is a condensation reaction of the product of the first step (formula Va) with an amine or alcohol of the general formula ($R^3R^4R^5N$) $(CH_2)_mZ$, with m as an integer from 1 to 12, wherein Z is $NH_2$, OH, or a secondary heterocyclic amine of the formula, wherein k and l are integers from 0 to 2, Or condensation reaction of the product of the first step (formula Vb or Vc) with carboxylic acid of the general formula ($R^3R^4R^5N$)$(CH_2)_mZ$, with m as an integer from 1 to 12, wherein Z is COOH.

$R^3$ and $R^4$ are either the same or different and independently $C_1$-$C_{12}$ alkyl, $C_1$-$C_{12}$ alkenyl, or $C_1$-$C_{12}$ alkynyl, which may be optionally substituted with a $C_1$-$C_6$ hydrocarbyl group, or $R^3$ and $R^4$ may join to form a ring of 3 to 10 carbon atoms and 0 to 6 heteroatoms chosen from nitrogen, thiol and oxygen, $R^5$ is either absent or is hydrogen or $C_1$-$C_{12}$ alkyl to provide a quaternary amine,
to yield a compound of the general formula (VI)

wherein n, m, Y, $R^1$, $R^2$, $R^3$, $R^4$ and $R^5$ are defined as above.

The second step is preferably performed at room temperature in a solvent such as dimethylformamide (DMF). In a preferred embodiment, N, N'-diisopropylcarbodiimide (DIC) is added to the reaction mixture.

The optional third step is an oxidation reaction of the thioether groups of the product of second step with an oxidising reagent to yield a compound of the general formula (I), wherein n, m, Y, $X^1$, $X^2$, $R^1$, $R^2$, $R^3$, $R^4$ and $R^5$ are defined as above. The third step is preferably performed at room temperature with aqueous hydrogen peroxide in a solvent such as methanol. The third step can further been catalyzed by a catalyst such as titanium-containing zeolites. This reaction has already been proposed by Hulea et al. (Hulea V, Moreau P, Renzo F D. Thioether oxidation by hydrogen peroxide using titanium-containing zeolites as catalysts. Journal of Molecular Catalysis A: Chemical. 1996, 111:325-332). Surprisingly this reaction does not affect other functional groups of the amino lipids of step b).

This reaction scheme is very versatile; it can be used to synthesize large libraries of cationic amino lipids for rapid cell-based screening assay in a very inexpensive manner. The resulting compounds all have both a hydrophobic character due to their long non-polar residues and a hydrophilic character due to their amino group. This amphiphilic character can be used to form lipid particles, e.g. lipid bilayers, micelles, liposomes, etc. Moreover, the amino group of these compounds confers a cationic charge which is useful for transfection agents. This library of different compounds with new characteristics can be tested easily for their transfection capacity of a wide variety of cell types.

Another embodiment of the present invention is directed to lipid particles containing an amino lipid of one of the claims 1 to 4. Within the scope of the invention, the term 'lipid particle' means nanosized objects made of amino lipids which are placed into an aqueous solution. These particles are inter alia lipid bilayer vesicles (liposomes), multi-lamellar vesicles or micelles.

In a preferred embodiment of the present invention, said nanoparticles are liposomes containing an amino lipid of one of the claims 1 to 4. Within the scope of the invention liposomes are microvesicles composed of a bilayer of lipid amphipathic (amphiphilic) molecules enclosing an aqueous compartment.

Liposome formation is not a spontaneous process. Lipid vesicles are formed first when lipids such as phospholipids are placed in water and consequently form one bilayer or a series of bilayers, each separated by water molecules. Liposomes can be created by sonicating lipid vesicles in water.

Within the scope of the invention, the term 'lipid bilayer' means a thin membrane made of two layers of lipid molecules. The term 'micelle' means an aggregate of surfactant molecules dispersed in a liquid colloid. A typical micelle in aqueous solution forms an aggregate with the hydrophilic head regions in contact with water, sequestering the hydrophobic single tail region in the micelle center.

Within the scope of the invention, the term 'cells' means a generic term and encompass the cultivation of individual cells, tissues, organs, insect cells, avian cells, fish cells, amphibian cells, mammalian cells, primary cells, continuous cell lines, stem cells and/or genetically engineered cells, such as recombinant cells expressing a heterologous polypeptide or protein. Recombinant cells include, for example, cells expressing heterologous polypeptides or proteins, such as a growth factor or a blood factor.

In a preferred embodiment said lipid particles or liposomes further contain a helper lipid. In a preferred embodiment said helper lipid is a non-cationic lipid. In a more preferred embodiment said helper-lipid is a non-cationic phospholipid. Within the scope of this invention, a non-cationic lipid may contain cationic functional groups (e.g. aminogroups) but it should contain anionic functional groups to at least neutralize the molecule. The totality of all functional groups in the lipid molecule should be non-cationic.

Liposomes consisting of a mixture of cationic amino lipids and non-cationic (neutral) phospholipids are the most effective for nucleic acid delivery into cells. In an even more preferred embodiment said non-cationic lipid is DOPE.

In a further preferred embodiment the lipid particle or liposome further comprises a sterol. Sterol, like cholesterol, is a natural component in cell membranes. It can be used to stabilise the particle, and help the integration with cell membrane.

In another embodiment of the invention, the lipid particles or liposomes further contain a bioactive agent. Within the scope of this invention a bioactive agent is one which has a biological effect when introduced into a cell or host, for example by stimulating an immune response or an inflammatory response, by exerting enzymatic activity or by complementing a mutation, etc. bioactive agents include inter alia nucleic acids, peptides, proteins, antibodies and small molecules.

When a liposome is used to encapsulate a drug substance either within the lipid bilayer or in the interior aqueous space of the liposome the term 'liposome drug' can be employed.

In a most preferred embodiment, the bioactive agent is a nucleic acid. In another preferred embodiment said bioactive agent is a member optionally selected from the group consisting of: an antineoplastic agent, an antibiotic, an immunomodulator, an anti-inflammatory agent, an agent acting on the central nervous system, a polypeptide or a polypeptoid.

In yet another embodiment the lipid particle or liposome further contains at least one polyethylene glycol (PEG)-lipid. PEG lipids help to protect the particles and their cargo from degradation in-vitro and in-vivo. Moreover, PEG form a protective layer over the liposome surface and increase the circulating time in vivo. It can be used in liposome drug delivery (PEG-liposome).

Lipid particles or liposomes containing a bioactive agent can be used to deliver any of a variety of therapeutic agents into cells. The present invention encompasses the use of lipid particles, especially liposomes, as described above for delivering a bioactive agent into a cell.

Preferably said bioactive agent is a nucleic acid, including but not limited to, RNA, antisense oligonucleotide, a DNA, a plasmid, a ribosomal RNA (rRNA), a micro RNA (miRNA), transfer RNA (tRNA), a small inhibitory RNA (siRNA) or small nuclear RNA (snRNA). The bioactive agent may also be an antineoplastic agent, an antibiotic, an immunomodulator, an anti-inflammatory agent, an agent acting on the central nervous system, antigens or fragments thereof, proteins, peptides, polypeptoid, vaccines and small-molecules or mixtures thereof.

As has been set out above, lipid particles or liposomes containing amino lipids as defined in the present invention are suitable to deliver bioactive agents into cells. The wide variety of different amino lipids which can be synthesised by the mentioned versatile synthesis method can be screened for particular characteristics that are conferred to the liposomes. Important characteristics are for example transfection efficiency, cytotoxicity, adhesion of the agent to be delivered into the cell, stability of the liposomes, size of the liposomes, etc. The present method allows the creation of specifically adapted liposomes for particular applications.

For example lipid particles (liposomes) can be used for transfecting multicellular tissues or organisms. This offers the possibility of a novel therapeutic treatment of patients.

According to the present invention, a patient can be any mammal, preferably selected from the group consisting of human, mouse, rat, pig, cat, dog, horse, goat, cattle, and monkey and/or others. Most preferably, the patient is a human being.

An important embodiment of the present invention is the use of said lipid particles or liposomes containing amino lipids according to one of formulas (I-III) for use as a medicament.

In particular, said lipid particles or liposomes can be administered to patients for use in gene therapy, in gene vaccination, in antisense therapy or in therapy by interfering RNA. A lipid particle of the invention may also be used for the manufacture of a medicine for use in nucleic acid transfer, for example in treatment of the human or animal body by therapy, especially in the treatment of a condition caused by or related to a genetic defect or modification.

Targets for gene therapy are well known and include monogenic disorders, for example, cystic fibrosis, various cancers, and infections, for example, viral infections, for example, with HIV. For example, transfection with the p53 gene offers great potential for cancer treatment. Targets for gene vaccination are also well known, and include vaccination against pathogens for which vaccines derived from natural sources are too dangerous for human use and recombinant vaccines are not always effective, for example, hepatitis B virus, human immunodeficiency virus (HIV), hepatitis C virus (HCV) and herpes simplex virus.

Targets for anti-sense therapy are also known. Further targets for gene therapy and anti-sense therapy are being proposed as knowledge of the genetic basis of disease increases, as are further targets for gene vaccination.

A lipid particle of the invention may be used in vaccination. Thus, a lipid particle or liposome of the invention may be used to deliver an antigen or a nucleic acid encoding an antigen. These techniques are familiar to a person skilled in the art. Examples for liposome vaccines are described in Butts C, et al. Randomized phase IIB trial of BLP25 liposome vaccine in stage IIIB and IV Non-Small-Cell Lung Cancer. Journal of Clinical Oncology. 2005, 23:6674-6681 and in U'Ren L, et al. Vaccination with liposome-DNA complexes elicits enhanced antitumor immunity. Cancer Gene Therapy. 2006, 13:1033-1044.

A lipid particle of the invention may be used to elicit an immune response against a wide variety of antigens for the treatment and/or prevention of a number of conditions including, but not limited to, cancer, allergies, toxicity and infection by pathogens such as viruses, bacteria, fungi, and other pathogenic organisms.

In a preferred embodiment of the invention said lipid particle or liposome can be used as a medicament in treatment of a viral infection, a liver disease or disorder, or cancer. On liver diseases, liposomes can be captured by the cells of the reticulo-endothelial system, which are primarily situated in the liver. The liposomes will be accumulated there.

SYNTHESIS

Example 1

Synthesis and characterization of N-(2-(dimethylamino)ethyl)-4,5-bis(dodecylthio)pentanamide (DEDPA)

The amino lipid was synthesized by two steps. The first step is to synthesize 4,5-bis(dodecylthio)pentanoic acid. 0.5 mmol pent-4-ynoic acid, 1 mmol dodecane-1-thiol and 5 mg 2,2-Dimethoxy-2-phenylacetonphenone (DMPA) were dissolved in 1.5 ml THF and added into a 20 ml glass vial covered with aluminium foil. The vial was degassed for 5 min and filled with Argon (Ar) for 3 min, then covered with a cap. The mixture was irradiated under UV 365 nm for 1 h and then the THF was transferred to a 50 ml flask and evaporated.

The second step is conjugation of 4,5-bis(dodecylthio)pentanoic acid with N1,N1-dimethylethane-1,2-diamine to get N-(2-(dimethylamino)ethyl)-4,5-bis(dodecylthio)pentanamide. 4,5-bis(dodecylthio)pentanoic acid from the first step was dissolved in 8 ml dichloromethane (DCM). 1 ml of this solution was diluted with 4 ml DCM and 11.61 µl N,N'-diisopropylcarbodiimide (DIC) (0.075 mmol, 1.2 eq.) were added. 0.063 mmol N1,N1-dimethylethane-1,2-diamine were added to the mixture and vortexed. Hydroxylbenzotriazole (HOBt) was dissolved in dimethylformamide (DMF) (304 mg in 608 µl DMF) and 19.45 µl of the HOBt solution were added. The vial was then covered with aluminium foil, and filled with Ar. After 16 h stirring the Dichloromethane (DCM) was evaporated, the residue was dissolved in 2 ml hexane and transferred into new vials. The product was separated by centrifugation and the supernatants were collected and the hexane was evaporated in desiccators. The product was sealed with Parafilm and stored under Ar.

To verify the identity of the molecules, crude product was analyzed by mass spectrometry. The molecular ion was clearly identified as 574.0 MW/z.

Synthesis of the compounds of the examples 2-7 were carried out similarly to example 1. Step 1 is performed in the same way. Step 2 differs in the educts, whereas the stoichiometric ratios were maintained. The resulting compounds and the corresponding MW/z values are summarized in Table 1:

TABLE 1

Examples of synthesized compounds 2-7 and the corresponding MW/z values.

| Example | Compound | MW/z |
|---|---|---|
| 2 | 4,5-bis(dodecylthio)-N-(2-morpholinoethyl)pentanamide | 614.8 |
| 3 | N-(2-(diethylamino)ethyl)-4,5-bis(dodecylthio)pentanamide | 600.0 |
| 4 | N-(3-(diethylamino)propyl)-4,5-bis(dodecylthio)pentanamide | 616.0 |
| 5 | 4,5-bis(dodecylthio)-N-(2-(pyrrolidin-1-yl)ethyl)pentanamide | 601.9 |
| 6 | N-(3-(dimethylamino)propyl)-4,5-bis(dodecylthio)pentanamide | 587.9 |

TABLE 1-continued

Examples of synthesized compounds 2-7 and the corresponding MW/z values.

| Example | Compound | MW/z |
|---|---|---|
| 7 | 1-(4-(2-(dimethylamino)ethyl)piperazin-1-yl)-4,5-bis(dodecylthio)pentan-1-one | 642.9 |

Example 8

Synthesis and characterization of N-(2-(dimethylamino)ethyl)-5,6-bis(dodecylthio)hexanamide The synthesis procedure of N-(2-(dimethylamino)ethyl)-5,6-bis(dodecylthio)hexanamide is similar to the previous examples.

The first step is to synthesize 5,6-bis(dodecylthio)hexanoic acid. 0.5 mmol hex-5-ynoic acid, 1 mmol dodecane-1-thiol and 5 mg DMPA were dissolved in 1.5 ml THF and added into a 20 ml glass vial. The vial was covered with aluminium foil, filled with Ar and irradiated under UV 365 nm for 1 h. Then the THF was transferred to a 50 ml flask and evaporated.

The second step is conjugating 5,6-bis(dodecylthio)hexanoic acid with N1,N1-dimethylethane-1,2-diamine to get N-(2-(dimethylamino)ethyl)-5,6-bis(dodecylthio)hexanamide. This step was carried out similar to the previous examples. The stoichiometric ratios were maintained.

To verify the identity of the molecules, crude product was tested by mass spectrometry (m/z 587.9).

Synthesises according to the examples 9-14 were carried out similarly to example 8. Step 1 is performed in an identical way. Step 2 differs in the educts, whereas the stoichiometric ratios were maintained. The resulting compounds and the corresponding molecular ion are resumed in table 2:

TABLE 2

Examples of synthesized compounds 9-14 and the corresponding MW/z values.

| Example | Compound | MW/z |
|---|---|---|
| 9 | 5,6-bis(dodecylthio)-N-(2-morpholinoethyl)hexanamide | 629.9 |

| 10 | N-(2-(diethylamino)ethyl)-5,6-bis(dodecylthio)hexanamide | 614.0 |

TABLE 2-continued

Examples of synthesized compounds 9-14 and the corresponding MW/z values.

| Example | Compound | MW/z |
|---|---|---|
| 11 | N-(3-(diethylamino)propyl)-5,6-bis(dodecylthio)hexanamide | 630.0 |
| 12 | 5,6-bis(dodecylthio)-N-(2-(pyrrolidin-1-yl)ethyl)hexanamide | 615.8 |
| 13 | N-(3-(dimethylamino)propyl)-5,6-bis(dodecylthio)hexanamide | 601.9 |
| 14 | 1-(4-(2-(dimethylamino)ethyl)piperazin-1-yl)-5,6-bis(dodecylthio)hexan-1-one | 657.1 |

Example 15

Synthesis and characterization of N-(2-(dimethylamino)ethyl)-4-(dodecylsulfinyl)-5-(dodecylthio)pentanamide The amino lipid is synthesized in one step. 1 mmol N-(2-(dimethylamino)ethyl)-4,5-bis(dodecylthio)pentanamide (DEDPA, product of example 1) was mixed with 10 mmol aqueous hydrogen peroxide (30%) in 10 ml methanol, and stirred at room temperature for 1 h. Then the mixture was transferred to a 50 ml flask and evaporated.

To verify the identity of the molecules, crude product was analyzed by mass spectrometry. The molecular ion was clearly identified as 589.7 MW/z.

Example 16

Synthesis and characterization of N-(2-(dimethylamino)ethyl)-4,5-bis(dodecylsulfonyl)pentanamide The amino lipid is synthesized in one step. 1 mmol N-(2-(dimethylamino)ethyl)-4,5-bis(dodecylthio)pentanamide (DEDPA, product of example 1) was mixed with 10 mmol aqueous hydrogen peroxide (30%) in 10 ml methanol, and stirred at room temperature for 2 d. Then the mixture was transferred to a 50 ml flask and evaporated.

To verify the identity of the molecules, crude product was analyzed by mass spectrometry. The molecular ion was clearly identified as 637.5 MW/z.

Screening of the Cationic Lipid for Cell Transfection

Example 17

Initial Determination of Optimal Lipid Ratios for Cell Transfection

The well documented HEK 293T cell line is used for examples 17 and 18.

The natural phospholipid dioleolylphosphatidylethanolamine (DOPE—structure shown below) was selected as the required co-lipid (also termed helper lipid). It is required not for the stability of liposomes per se, but rather the breakdown of the lipid membranes in the endocytic compartment (endosomes) of cells, allowing release of the bioactive agent to the cytosol and/or nucleus. Basically, it is required for the desired effect for stable liposome formation in combination with our cationic amino lipid (DEDPA). DOPE was mixed with a representative cationic amino lipid (structure shown below) in different ratios. Both lipids were dissolved in ethanol at 50 mg/ml and combined to a final volume of 30 µl.

DOPE

Neutral Helper Lipid

N-(2-(dimethylamino)ethyl)-4,5-bis(dodecylthio) pentanamide (DEDPA) as representative novel cationic amino lipid

TABLE 3

DEDPA:DOPE ratios tested

| DEDPA | DOPE |
| --- | --- |
| 0 | 1 |
| 1 | 3 |
| 1 | 2 |
| 1 | 1 |
| 2 | 1 |
| 3 | 1 |
| 1 | 0 |

These 30 μl ethanol mixtures were then added to 70 μl of 0.2 M Sodium acetate buffer (pH 5.0) with constant vortexing for 30 s, followed by sonication for 5 min to form liposomes. Final lipid content is 2 mg/ml. This final 2 mg/ml liposome sample is referred to as the "lipid reagent".

0.1 μl, 0.2 μl, 0.3 μl, 0.4 μl and 0.5 μl of the above lipid reagents were combined with either 50 ng or 100 ng plasmid DNA (comprising the pCS-LacZ and pEGFP-C1 plasmids at a ratio of 9:1, respectively) and mixed with cells as described below:

(amounts shown are for one well of a 96-well culture plate)
1. 0.1 μl-0.5 μl lipid reagent diluted in 10 μl of 50 mM sodium acetate buffer, pH 5.0
2. After 2-5 min incubation, added diluted lipid reagent from (1) to either 50 ng or 100 ng plasmid DNA (DNA dissolved in 10 μl of 50 mM sodium acetate buffer, pH 5.0).
3. Samples were left at RT for 30 min to form Lipid/DNA transfection complexes. As DNA is negatively charged, it associates non-specifically with the positively charged head groups of the cationic lipids in the liposomes.
4. After 30 min, 50 μl of freshly suspended HEK 293 cells (approximately 50,000 cells, in DMEM culture medium supplemented with 10% foetal calf serum) were added to the lipid/DNA complexes, mixed with pipette action and 65 μl of the cells+lipid/DNA complexes added to a single 96-well.

To assess the ability of the lipid mixtures to deliver the plasmid DNA into cells, microscopy was used to visualize fluorescence emitted by the green fluorescent protein (GFP) 20-24 hours after initial transfection. The GFP protein is encoded by the pEGFP-C1 plasmid and is efficiently synthesized and located within the cytoplasm of successfully transfected cells.

Results:

An optimal ratio of amino lipid:DOPE was identified as 1:1 and the optimal lipid reagent:DNA ratio was 0.4 μl lipid reagent per 50 ng DNA. These conditions were therefore used for the primary screen to identify the lipid reagents with highest cell transfection efficiency and lowest cell toxicity, as described in example 18 below.

Example 18

Primary Screen Using Novel Lipids Reagents

Cell line: HEK 293 cells
Screen format: 96-well
Detection (read-out): GFP fluorescence relative to total cell number (total cell number assessed using the nuclear dye, Hoechst—see FIG. 1)
A commercially available liposomal transfection reagent was used as a reference (reference reagent) according to manufacturers' instructions, see FIG. 1.

Method:
All steps performed in 96 tube/plate format using 8- or 12-channel multipipettes. Amounts shown are for duplicate (2×) wells of a 96-well plate.
1. 0.8 μl lipid reagents diluted in 20 μl 50 mM NaOAc buffer, pH 5.0.
2. Diluted lipid reagents from (1) were added to 100 ng DNA (10 ng pEGFP-C1+90 ng pCS-LacZ plasmids) in 20 μl NaOAc buffer, pH 5.0 and mixed with pipette action.
3. After 30 min incubation at RT, added 100 μl freshly resuspended cells ($3-5\times10^5$ cells/50 μl DMEM culture medium supplemented with 10% foetal calf serum) and mixed with pipette.
4. Duplicate 65 μl aliquots of the cells+lipid/DNA complexes were immediately transferred to separate wells of a 96-well culture plate and placed in 37° C. incubator with 5% $CO_2$.
5. After 5 hours, added 50 μl fresh cell culture medium (DMEM supplemented with 10% FCS).
6. 20 to 24 hours after initial transfection of cells, Hoechst 33258 dye was added to cells at a final concentration of 0.2 μg/ml and cells incubated for a further 30 min at 37° C. Cells were then placed on an inverted microscope and 2 independent sets of images of the cells captured from each well as shown in FIG. 1.

Figure 1:
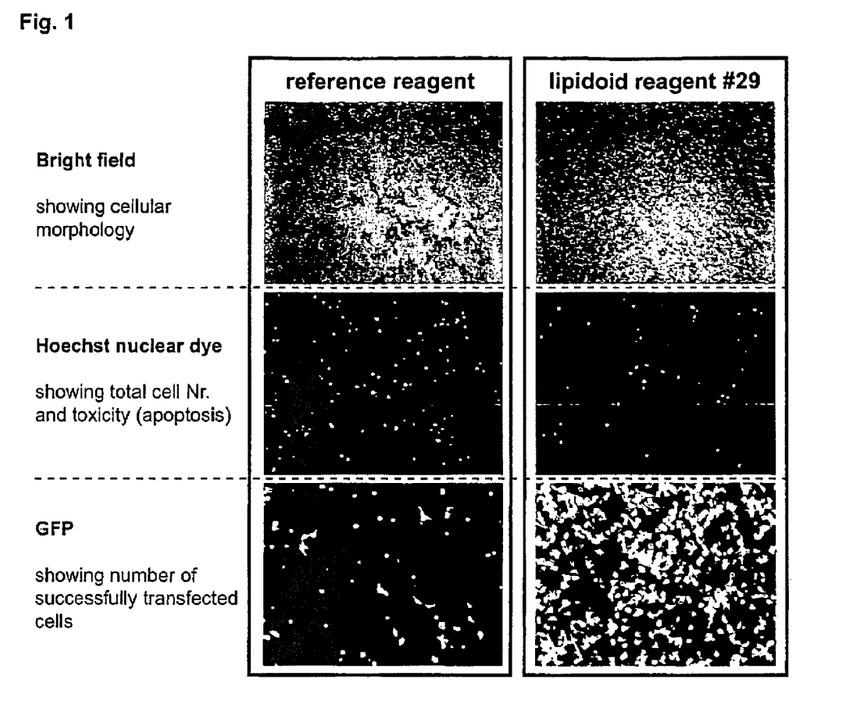
FIG. 1 shows comparative microscope pictures showing results of lipofection by use of an amino liposomal reagent and two commercially available transfection reagents.

For each sample, 3 images were captured: bright field image of cells (FIG. 1 upper panels), Hoechst dye stained image of total cell nuclei (FIG. 1 middle panels) and GFP images showing cells successfully transfected with plasmid DNA and expressing GFP protein (FIG. 1 lower panels).

Microscope images of transfected HEK 293 cells, showing both the transfection efficiency and toxicity level of one of our lipid molecules (#29) compared to a commonly used commercial transfection reagent (reference reagent). Lipid reagent #29 has a transfection efficiency of approximately 95% and has low cell toxicity (very few brightly stained apoptotic nuclei). In general, the greater the transfection efficiency of liposomal reagents, the greater is the cellular toxicity. This is obvious for the reference reagent, where a high percentage of cells are transfected but, as a consequence, there are many unhealthy and apoptotic cells.

Figure 2:
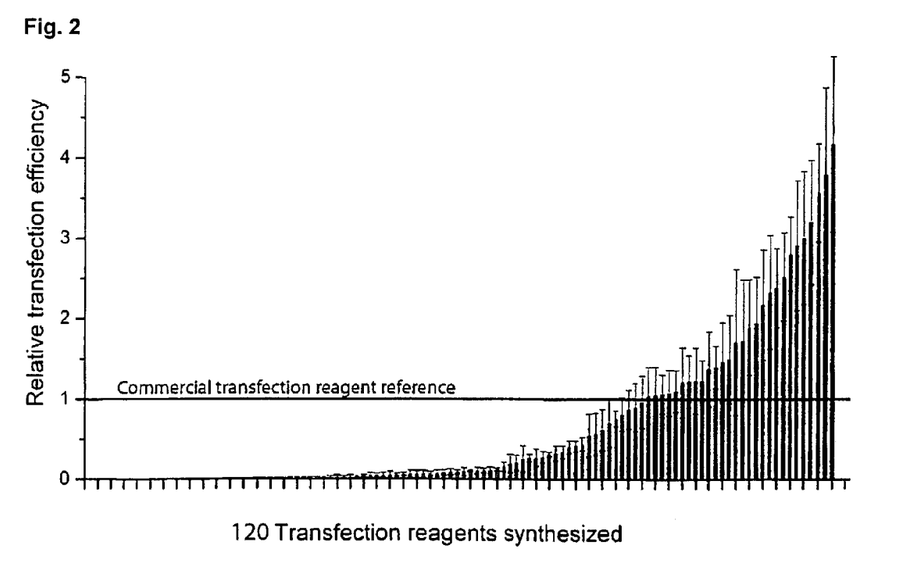
FIG. 2 shows a graphical overview of the transfection efficiency of a library of 120 transfection reagents compared to a commercially available reagent.

Note the increased number of cells showing a GFP signal as well as the reduced toxicity. Toxicity is seen by a reduction in total cell number as well as an increase in apoptotic cells, which are detected as brightly stained cells after Hoechst staining According to the protocol given in Example 18, a library of 120 newly synthesized compounds according to claim 1 have been tested for their ability to transfect HEK 293 cells. The graph in FIG. 2 shows the transfection efficiency of these lipid compounds compared to a commercially available transfection agent reference. 15 of the lipid molecules are significantly more efficient at delivering plasmid DNA (GFP gene) to HEK 293 cells when compared to a widely used commercial transfection reagent, indicated by the solid line. Of these 15 highly efficient new transfection reagents, one in particular has been identified as possessing very low toxicity and has the ability to very efficiently deliver siRNA molecules to cells (#29; see FIG. 1 and FIG. 3).

Example 19

Screen of Library "Hits" for Ability to Transfect siRNA

One of the key technologies for manipulation of gene function, both in cells and whole organisms, is gene silencing through RNA interference (RNAi). Delivery of small interfering RNA (siRNA) molecules into mammalian cells is crucial for this technology and has significant clinical/therapeutic implications.

Thus, in addition to screening our lipids for delivery of plasmid DNA (the genes) we have also screened amino lipids according to the present invention for their ability to efficiently deliver siRNA molecules (the gene silencers).

In order to screen for this two different types of cells were used to test the ability of our lipid reagents to deliver siRNA targeting Low density lipoprotein receptor related protein 6 (LRP6). This is a 200 kD single-pass transmembrane receptor for Wnt ligands and activates the Wnt/b-catenin signalling pathway. It is expressed at relatively low levels in HEK 293 cells and relatively high levels in MEF cells.

Assay 1. Transfection of siRNA in HEK 293 Cells
Method:
All steps performed in 1.5 ml eppendorf tubes and 24 well plate format. Amounts shown are for one well of a 24-well plate.
1. 2 µl lipid reagents diluted in 50 µl 50 mM NaOAc buffer, pH 5.0.
2. Diluted lipid reagents from (1) added to 20 pmol (1 µl of 20 uM) siRNA molecules in 241 NaOAc buffer, pH 5.0 and mixed with pipette action. The siRNA molecules used had either a scrambled sequence not specific for any known gene (Con siRNA), or a sequence specifically targeting the endogenous mRNA from the LRP6 gene (LRP6 siRNA).
3. After 30 min incubation at RT, added 400 µl freshly resuspended cells (3-5×10$^5$ cells/50 µl DMEM culture *medium* supplemented with 10% foetal calf serum) and mixed with pipette.
4. Lipid/siRNA complexes were immediately transferred to separate wells of a 24-well culture plate and placed in 37° C. incubator with 5% CO$_2$.
5. 48 hours after initial transfection, cells, were lysed in 50 µl detergent buffer (50 mM Tris, 1% Triton X-100, 0.15 M NaCl, pH7.0, containing protease and phosphatase inhibitors), spun to remove insoluble cell debris and 30 ul clarified lysates added to 10 µl of 4×SDS loading buffer (250 mM Tris HCl, 40% Glycerol, 8% SDS, 0.01% Bromophenol Blue, 5% 2-Mercaptoethanol, pH 6.8).
6. Samples were denatures by heating at 96° C. for 2 min. and 10 µl loaded on a 9% SDS-PAGE gels for separation of proteins according to molecular weight. Separated proteins were transferred from the SDS-PAGE gel to nitrocellulose membrane for Western Blot (WB) analysis.
7. WB was performed using an automated BioLane HTI instrument using an antibody against LRP6. An HRP linked secondary antibody and chemiluminescence was used to detect the proteins on the membrane.

Assay 2. Transfection of siRNA in Mouse Embryonic Fibroblast (MEF) Cells
Method:
All steps performed in 1.5 ml Eppendorf tubes and 24 well plate format. Amounts shown are for one well of a 24-well plate.
1. 2 µl lipid reagents diluted in 50 µl 50 mM NaOAc buffer, pH 5.0.
2. Diluted lipid reagents from (1) added to 20 pmol (1 µl of 20 µM) siRNA molecules in 20 µl NaOAc buffer, pH 5.0 and mixed with pipette action. The siRNA molecules used had either a scrambled sequence not specific for any known gene (Con siRNA), or a sequence specifically targeting the endogenous mRNA from the LRP6 gene (LRP6 siRNA).
3. After 30 min incubation at RT, added 400 µl fresh DMEM culture medium supplemented with 10% foetal calf serum, mixed with pipette and added to adherent MEF cells (50-70% confluency) in one well of a 24-well plate and placed in 37° C. incubator with 5% CO$_2$.
4. 48 hours after initial transfection, cells, were lysed in 100 µl detergent buffer (50 mM Tris, 1% Triton X-100, 0.15 M NaCl, pH 7.0, containing protease and phosphatase inhibitors), spun to remove insoluble cell debris and 30 µl clarified lysates added to 10 µl of 4×SDS loading buffer (250 mM Tris HCl, 40% Glycerol, 8% SDS, 0.01% Bromophenol Blue, 5% 2-Mercaptoethanol, pH 6.8).
5. Samples were denatures by heating at 96° C. for 2 min and 5 µl loaded on a 9% SDS-PAGE gels for separation of proteins according to molecular weight. Separated proteins were transferred from the SDS-PAGE gel to nitrocellulose membrane for Western Blot (WB) analysis.
6. WB was performed using an automated BioLane HTI instrument using antibodies against LRP6 and beta-actin proteins. HRP linked secondary antibodies and chemiluminescence were used to detect the proteins on the membrane.

Results

Figure 3:
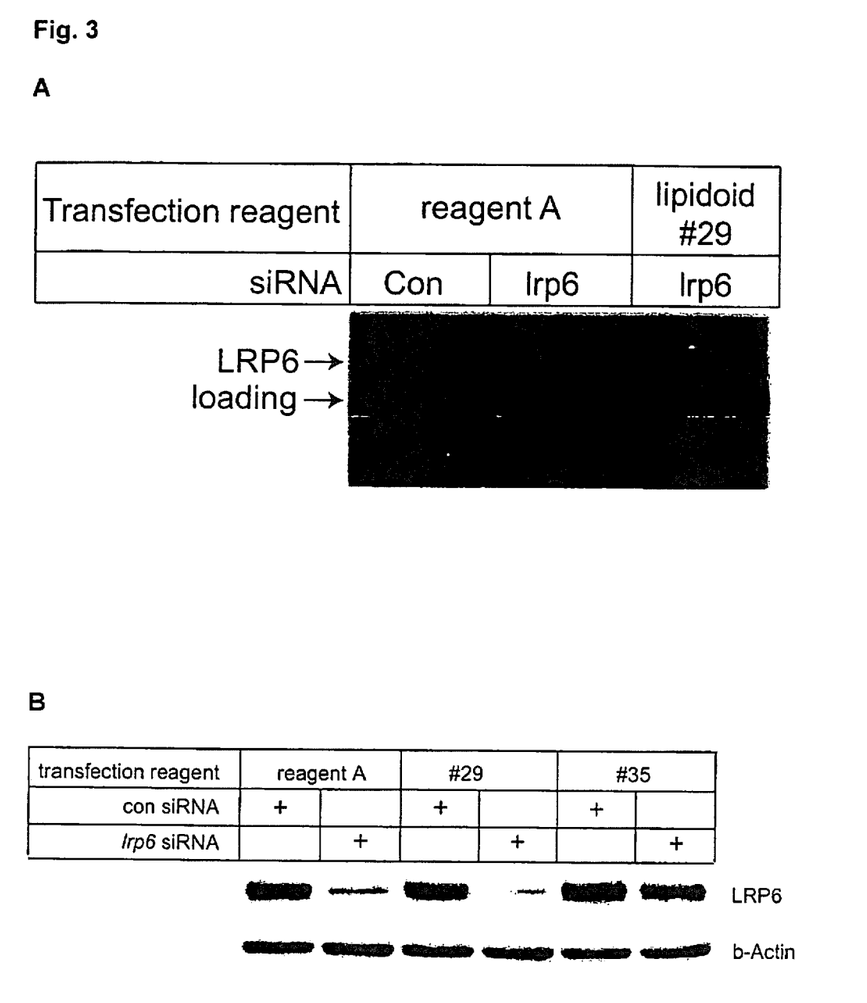
FIG. 3 shows siRNA gene silencing in HEK 293 and MEF cells.

FIG. 3 A shows a Western Blot (WB) analysis of endogenous LRP6 protein from total lysates of 293 cells transfected with the indicated siRNA molecules and incubated for 48 hours. The endogenous level of LRP6 is strongly downregulated after LRP6 siRNA delivery using reagent A, however this effect is stronger using a lipid reagent according to this invention #29. Con refers to a non-targeting, scrambled siRNA control and loading refers to a non-specific protein band that is used as a reference to show that similar protein amounts were loaded for each sample (thus demonstrating specific silencing of the siRNA target).

FIG. 3 B shows the Western Blot (WB) analysis of LRP6 protein from total lysates of MEF (mouse embryonic fibroblast) cells transfected with the indicated siRNA molecules and cultured for 48 hours. Again lipid reagent #29 is more effective than the commercial reagent A at siRNA mediated gene silencing. A second lipid reagent (#35) is also shown that has little effect, despite the fact that it can efficiently transfect cells with plasmid DNA. This demonstrates the striking difference in properties of related transfection reagents and highlights the importance of using our novel method to easily synthesise hundreds of related lipids that can be screened to identify the ones having optimal properties (such as highly efficient DNA and siRNA delivery as well as low cellular toxicity).

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

LIST OF ABBREVIATIONS

Ar Argon
DCM Dichloromethane
DEDPA N-(2-(Dimethylamino)ethyl)-4,5-bis(dodecylthio) pentanamide
DIC N, N'-Diisopropylcarbodiimide
DMEM Culture medium
DMF Dimethylformamide
DMPA 2,2-Dimethoxy-2-phenylacetonphenone
DNA Desoxyribonucleic acid
DOPE Dioleolylphosphatidylethanolamine
EGFP Enhanced GFP
GFP Green Fluorescent Protein
HOBt Hydroxylbenzotriazole HRP Horseradish Peroxidase
kD kilo Dalton
LRP6 Low density lipoprotein receptor related protein 6
MEF Mouse embryonic fibroblast
PEG Polyethylene glycol
RNA Ribonucleic acid
RNAi RNA interference
siRNA small interfering RNA
SDS Sodium dodecyl sulfate
THF Tetrahydrofuran
WB Western Blot
Wnt Signalling proteins in cell differentiation

The invention claimed is:
1. An amino lipid having the structure of Formula (I):

(I)

wherein:
  $R^1$ and $R^2$ are the same or different, each of $R^1$ and $R^2$ being selected from one of $C_6$-$C_{24}$ alkyl, $C_6$-$C_{24}$ alkenyl, $C_6$-$C_{24}$ alkynyl, and $C_6$-$C_{24}$ acyl;
  $X^1$ and $X^2$ are the same or different, each of $X^1$ and $X^2$ being selected from one of S, S=O, and S(=O)$_2$;
  Y is selected from one of an amide, an ester, and a heterocyclic amide of the formula:

wherein:
  $R^3$ and $R^4$ are the same or different, each of $R^3$ and $R^4$ being selected from one of $C_1$-$C_{12}$ alkyl, $C_1$-$C_{12}$ alkenyl, and $C_1$-$C_{12}$ alkynyl, or $R^3$ and $R^4$ join to form a substituted heterocyclic ring of 3 to 10 atoms and 1 to 6 heteroatoms selected from one of nitrogen, thiol and oxygen;
  $R^5$ is omitted or selected from one of hydrogen and $C_1$-$C_{12}$ alkyl to provide a quaternary amine;
  k is an integer from 0 to 2;
  l is an integer from 0 to 2;
  m is an integer from 1 to 12; and
  n is an integer from 2 to 12.

2. The amino lipid according to claim 1, wherein said $C_6$-$C_{24}$ alkyl, $C_6$-$C_{24}$ alkenyl, $C_6$-$C_{24}$ alkynyl, and $C_6$-$C_{24}$ acyl are substituted with a $C_1$-$C_6$ hydrocarbyl group.

3. The amino lipid according to claim 1, wherein said $C_1$-$C_{12}$ alkyl, $C_1$-$C_{12}$ alkenyl, and $C_1$-$C_{12}$ alkynyl are substituted with a $C_1$-$C_6$ hydrocarbyl group.

4. The amino lipid according to claim 1, wherein $R^1$ and $R^2$ are each said $C_6$-$C_{24}$ alkyl, or a $C_1$-$C_6$ hydrocarbyl group.

5. The amino lipid according to claim 1 having the structure of Formula (II):

(II)

wherein:
  $R^1$ and $R^2$ are each the same $C_6$-$C_{18}$ alkyl;
  Y is selected from one of an amide, an ester and a heterocyclic amide of the formula:

$R^3$ and $R^4$ are either the same or different $C_1$-$C_{12}$ alkyls, or $R^3$ and $R^4$ join to form a substituted heterocyclic ring of 3 to 10 atoms and 1 to 6 heteroatoms selected from one of nitrogen, thiol and oxygen;
  m is an integer from 1 to 12; and
  n is an integer from 2 to 12.

6. The amino lipid according to claim 5, wherein said $C_1$-$C_{12}$ alkyl is substituted with a $C_1$-$C_6$ hydrocarbyl group.

7. The amino lipid according to claim 1, having a structure selected from one of Formula (IIIa), (IIIb) and (IIIc):

(IIIa)
(IIIb)
(IIIc)

wherein:
  $R^1$ and $R^2$ are each the same $C_{11}$-$C_{12}$ alkyls;
  $R^3$ and $R^4$ are each the same $C_1$-$C_2$ alkyls;
  m is an integer from 1 to 2; and
  n is an integer from 2 to 3.

8. A method to synthesize an amino lipid of Formula (I):

(I)

comprising the steps of:
performing a reaction of alkynes of the Formula (IVa), (IVb) or (IVc):

(IVa)

(IVb)

(IVc)

with compounds of the formula, HS—$R^1$ and HS—$R^2$, to yield a compound of the Formula (Va), (Vb) or (Vc):

(Va)

(Vb)

(Vc)

under UV-irradiation or by using a radical initiator, wherein:
$R^1$ and $R^2$ are the same or different, each of $R^1$ and $R^2$ being selected from $C_6$-$C_{24}$ alkyl, $C_6$-$C_{24}$ alkenyl, $C_6$-$C_{24}$ alkynyl and $C_6$-$C_{24}$ acyl, and n is an integer from 2 to 12; and
performing a condensation reaction of the compound of the Formula (Va) with an amine or alcohol of the formula $(R^3R^4R^5N)(CH_2)_mZ$, wherein:
Z is $NH_2$, OH, or a secondary heterocyclic amine of the formula:

k is an integer from 0 to 2;
l is an integer from 0 to 2; and m as an integer from 1 to 12;
or
performing a condensation reaction of the compound of the Formula (Vb) or (Vc) with carboxylic acid of the formula $(R^3R^4R^5N)(CH_2)_mZ$, wherein:
Z is COOH;
$R^3$ and $R^4$ are the same or different, each of $R^3$ and $R^4$ being selected from $C_1$-$C_{12}$ alkyl, $C_1$-$C_{12}$ alkenyl and $C_1$-$C_{12}$ alkynyl, or $R^3$ and $R^4$ join to form a ring of 3 to 10 carbon atoms and 1 to 6 heteroatoms selected from one of nitrogen, thiol and oxygen; and
$R^5$ is omitted or selected from one of hydrogen and $C_1$-$C_{12}$ alkyl to provide a quaternary amine;
to yield a compound of the Formula (VI):

(VI)

9. The method of claim 8, wherein said $C_6$-$C_{24}$ alkyl, $C_6$-$C_{24}$ alkenyl, $C_6$-$C_{24}$ alkynyl and $C_6$-$C_{24}$ acyl are substituted with a $C_1$-$C_6$ hydrocarbyl group.

10. The method of claim 8, wherein said $C_1$-$C_{12}$ alkyl, $C_1$-$C_{12}$ alkenyl and $C_1$-$C_{12}$ alkynyl are substituted with a $C_1$-$C_6$ hydrocarbyl group.

11. The method according to claim 8, further comprising oxidizing thioethers of the Formula (VI) into at least one sulfoxide (S=O) and sulfone (S(=O)$_2$) using an oxidation reagent.

12. A lipid particle comprising the amino lipid of Formula (I) in claim 1.

13. A lipid particle comprising the amino lipid of Formula (II) in claim 5.

14. A lipid particle comprising the amino lipid of Formula (IIIa), (IIIb), or (IIIc) in claim 7.

15. The lipid particle of claim 12, wherein said lipid particle is a liposome.

16. The lipid particle of claim 12, further comprising a non-cationic lipid.

17. The lipid particle of claim 12, further comprising a sterol.

18. The lipid particle of claim 12, further comprising a bioactive agent.

19. The lipid particle of claim 18, wherein said bioactive agent is a member selected from the group consisting of a nucleic acid, an antineoplastic agent, an antibiotic, an immunomodulator, an anti-inflammatory agent, an agent acting on a central nervous system, a polypeptide or a polypeptoid.

20. A method of using the lipid particle of claim 18 as a vehicle for delivering said bioactive agent into a cell.

21. A method of administering a medicament to a human using the lipid particle of claim 12.

22. The method of claim 21, wherein the medicament is used in treatment of at least one of a viral infection, a liver disease or disorder, or cancer.

* * * * *